United States Patent [19]

Wirth et al.

[11] Patent Number: 5,073,277

[45] Date of Patent: Dec. 17, 1991

[54] LUBRICANTS CONTAINING AMMONIUM SALTS OF METHYLPHOSPHONIC ACID

[75] Inventors: Hermann O. Wirth, Bensheim; Klaus Müller, Lörrach, both of Fed. Rep. of Germany

[73] Assignee: Ciba-Geigy Corporation, Ardsley, N.Y.

[21] Appl. No.: 558,974

[22] Filed: Jul. 26, 1990

Related U.S. Application Data

[60] Division of Ser. No. 343,222, Apr. 26, 1989, Pat. No. 4,962,227, which is a division of Ser. No. 161,374, Feb. 22, 1988, Pat. No. 4,847,457, which is a division of Ser. No. 18,855, Feb. 24, 1987, abandoned, which is a continuation of Ser. No. 702,294, Feb. 15, 1985, abandoned.

[30] Foreign Application Priority Data

Feb. 24, 1984 [CH] Switzerland ............................. 911/84

[51] Int. Cl.$^5$ ................. C10M 137/12; C10M 137/14
[52] U.S. Cl. ............................... 252/32.7 R; 252/32.5
[58] Field of Search ........................ 252/32.5, 32.7 R

[56] References Cited

U.S. PATENT DOCUMENTS

| 3,609,077 | 9/1971 | Breitigam | 252/32.5 |
| 4,847,457 | 7/1989 | Wirth et al. | 252/32.5 |
| 4,962,227 | 10/1990 | Wirth et al. | 252/32.5 |

FOREIGN PATENT DOCUMENTS

| 543685 | 7/1957 | Canada | 252/32.5 |
| 546699 | 9/1957 | Canada | 252/32.5 |
| 594985 | 3/1960 | Canada | 252/32.5 |

*Primary Examiner*—Prince Willis, Jr.
*Assistant Examiner*—Ellen McAvoy
*Attorney, Agent, or Firm*—Harry Falber

[57] ABSTRACT

Novel salts of methylphosphonic acid with primary amines are described. These compounds are preferably used as extreme pressure additives in lubricant compositions.

1 Claim, No Drawings

LUBRICANTS CONTAINING AMMONIUM SALTS OF METHYLPHOSPHONIC ACID

This is a divisional of application Ser. No. 343,222 filed on Apr. 26, 1989, now U.S. Pat. No. 4,962,227,; which is a divisional of Ser. No. 161,374 filed on Feb. 22, 1988, now U.S. Pat. No. 4,847,457, which is a divisional of 018,855 filed on Feb. 24, 1987, now abandoned, which is a continuation of Ser. No. 702,294 filed on Feb. 15, 1985, now abandoned.

The present invention relates to novel ammonium salts of methylphosphonic acid and to the use thereof as additives for lubricants, as well as to compositions containing these novel compounds and to a process for lubricating machine parts.

Ammonium salts of methylphosphonic acid suitable for use as antiwear and high pressure additives for water-miscible hydraulic liquids are known from European patent application 12106. The ammonium cation of these compounds contains at least one $\beta$-hydroxyethyl group, which imparts to the salts solubility in polar liquids.

$\alpha$-Chloromethylphosphonic acids in combination with primary alkylamines, the alkyl moiety of which contains more than 8 carbon atoms and is preferably branched, are disclosed as extreme pressure additives in U.S. Pat. No. 2,858,332. Depending on the end use, the monoamino or diamino derivative is preferably used.

Surprisingly, it has now been found that salts of methylphosphonic acid with primary amines, in particular salts which contain less than 2 equivalents of amine, impart unusually good extreme pressure properties to lubricants. These compounds are even superior in this respect to the very effective known thiaphosphetane derivatives.

Specifically, the present invention relates to compounds of formula I

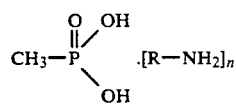
(I)

wherein n is an integer from 1.0 to 2.2 and R is a straight chain or branched $C_8$-$C_{30}$ alkyl group which may be interrupted by 1 to 5 sulfur atoms, or R is straight chain or branched $C_8$-$C_{30}$ alkenyl.

R as straight chain $C_8$-$C_{30}$ alkyl is n-octyl, n-decyl, n-undecyl, n-dodecyl, n-tridecyl, n-tetradecyl, n-hexadecyl, n-octadecyl, n-eicosyl, n-docosyl or n-triacontyl. R as branched $C_8$-$C_{30}$ alkyl may be 1,1,3,3-tetramethylbutyl, 1,1,3,3,5,5-hexamethylhexyl, 1,1,3,3,5,5,7,7-octamethyloctyl or 1,1,3,3,5,5,7,7,9,9-decamethyldecyl.

A suitable value for R as $C_8$-$C_{30}$ alkenyl is in particular oleyl. It is preferred to use primary amines containing a branched $C_8$-$C_{30}$ alkyl radical R, in particular those containing tertiary carbon atoms and, most preferably, those containing a tertiary carbon atom in the $\alpha$-position relative to the amino group. These amines can be obtained for example from branched primary alcohols which are obtained in the Oxo process in accordance with known methods. Such reactions are described by P. W. Sherwood in the Oil and Gas Journal, 1949, 71. It is preferred to use mixtures of those amines which are commercially available under the trade name of "Primenes". Thus, for example, it is possible to use the mixture "Primene ® 81-R" (principally branched alkylamines containing 12 to 15 carbon atoms) or the mixture "Primene ® JM-T" (principally branched primary alkylamines containing 18 to 24 carbon atoms).

A further preferred value for R is $C_8$-$C_{30}$ alkyl which is interrupted by 1 to 5 sulfur atoms, in particular branched $C_8$-$C_{30}$ alkyl which is interrupted by 1 to 5 sulfur atoms. Most preferably R is $-CH_2CH_2-S-$alkyl ($C_9$-$C_{12}$), in particular $-CH_2-CH_2-S-t-C_{12}H_{25}$ and $-CH_2-CH_2-S-t-C_9H_{19}$. By $t-C_9H_{19}$ and $t-C_{12}H_{25}$ are meant a mixture of different isomers which are preferably characterised in that a tertiary carbon atom is in the $\alpha$-position. It will be appreciated that the $C_9$-$C_{12}$ alkyl radical can also denote a mixture of branched alkyl radicals containing a different number of carbon atoms.

Also preferred are compounds of formula I, wherein n is 1.0 to 1.5 or wherein R is $C_{10}$-$C_{30}$ alkyl, preferably branched alkyl which carries a tertiary carbon atom in the $\alpha$-position relative to the amino group.

The compounds of formula I can be prepared in a manner known per se. The simplest procedure comprises reacting methylphosphonic acid of formula II

(II)

with an amine of formula III

R—NH$_2$ (III)

wherein R is as defined above. The molar ratio is preferably 1:1 to 1:2.2, preferably 1:1.5. If appropriate, a solvent or diluent is used, for example an alcohol such as methanol, which can be distilled off, e.g. under reduced pressure, upon completion of the reaction. The amine salt is obtained as a viscous oil.

The starting materials employed are known compounds which can be obtained in simple manner.

The compounds of formula I are employed in concentrations of 0.01 to 10% by weight, based on the total weight of the lubricant formulation. The preferred concentration range is from 0.05 to 5.0% by weight.

By virtue of their properties for effecting an enhancement of extreme pressure and antiwear performance, the compounds of this invention are suitable additives for synthetic lubricating oils or greases as well as for mineral oil-based lubricating compositions. The compounds of formula I can also be used in oils for processing metals. Accordingly, the invention also relates to lubricating compositions which contain compounds of formula I as well as to the use of compounds of formula I as extreme pressure and antiwear additives in lubricating compositions. Further, the invention relates to a process for lubricating machine parts which are subject to severe shock stress, which process comprises the use of a lubricant composition which contains a compound of formula I.

Suitable lubricant compositions are known to the skilled person and are described for example in "Schmiermittel-Taschenbuch," Hüthig Verlag, Heidelberg, 1974. In addition to mineral oils, particularly suitable lubricants are for example poly-$\alpha$-olefins, carboxylate-based lubricants, phosphate esters, polyalkylene glycols and mixtures of said lubricants.

The lubricant compositions can also contain other additives in order to enhance certain use properties, for example further antioxidants, metal passivators, rust inhibitors, viscosity index improvers, pour-point depressors, dispersants/surfactants and antiwear additives.

EXAMPLES OF PHENOLIC ANTIOXIDANTS

1. Alkylated monophenols
2,6-di-tert-butylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-dicyclopentyl-4-methylphenol
2-(α-methylcyclohexyl)-4,6-dimethylphenol
2,6-di-octadecyl-4-methylphenol
2,4,6-tricyclohexylphenol
2,6-di-tert-butyl-4-methoxymethylphenol 2. Alkylated hydroquinones
2,6-di-tert-butyl-4-methoxyphenol
2,5-di-tert-butyl-hydroquinone
2,5-di-tert-amyl-hydroquinone
2,6-diphenyl-4-octadecyloxyphenol 3. Hydroxylated thiodiphenyl ethers
2,2'-thio-bis(6-tert-butyl-4-methylphenol)
2,2'-thio-bis(4-octylphenol)
4,4'-thio-bis(6-tert-butyl-3-methylphenol)
4,4'-thio-bis(6-tert-butyl-2-methylphenol)

4. Alkylidene bisphenols
2,2'-methylene-bis(6-tert-butyl-4-methylphenol)
2,2'-methylene-bis(6-tert-butyl-4-ethylphenol)
2,2'-methylene-bis[4-methyl-6-(α-methylcyclohexyl)-phenol]
2,2'-methylene-bis(4-methyl-6-cyclohexylphenol)
2,2'-methylene-bis(6-nonyl-4-methylphenol)
2,2'-methylene-bis(4,6-di-tert-butylphenol)
2,2'-ethylidene-bis(4,6-di-tert-butylphenol)
2,2'-ethylidene-bis(6-tert-butyl-4-isobutylphenol)
2,2'-methylene-bis[6-(α-methylbenzyl)-4-nonylphenol]
2,2'-methylene-bis[6-(α,α-dimethylbenzyl)-4-nonylphenol]
4,4'-methylene-bis(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5'-tert-butyl-4'-hydroxy-2'-methylphenyl)-3-n-dodecylmercaptobutane
ethyleneglycolbis[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methylbenzyl)-6-tert-butyl-4-methylphenyl]terephthalate.

5. Benzyl Compounds
1,3,5-tri-(3',5'-di-tert-butyl-4'-hydroxybenzyl)-2,4,6-trimethylbenzene
di-(3,5-di-tert-butyl-4-hydroxybenzyl)sulfide
bis-(4-tert-butyl-3-hydroxy-2,6-dimethylbenzyl)dithiolterephthalate
1,3,5-tris(3',5'-di-tert-butyl-4'-hydroxybenzyl)isocyanurate
1,3,5-tris-(4'-tert-butyl-3'-hydroxy-2',6'-dimethylbenzyl)isocyanurate
dioctadecyl 3,5-di-tert-butyl-4-hydroxybenzylphosphate
calcium salt of monoethyl 3,5-di-tert-butyl-4-hydroxybenzylphosphonate 6. Acylaminophenols
4-hydroxylauric anilide
4-hydroxystearic anilide
2,4-bisoctylmercapto-6-(3',5'-tert-butyl-4'-hydroxyanilino)-s-triazine
octyl-N-(3,5-di-tert-butyl-4-hydroxyphenyl)carbamate 7. Esters of β-(3,5-di-tert-butyl-4-hydroxyphenyl)-propionic acid with monohydric or polyhydric alcohols, for example with methanol, octadecanol, 1,6-hexanediol, neopentyl glycol, thiodiethylene glycol,diethyleneglycol, triethylene glycol, pentaerythritol, trishydroxyethyl isocyanurate, dihydroxyethyloxalyldiamide.

8. Esters of β-(5-tert-butyl-4-hydroxy-3-methylphenyl)propionic acid with monohydric or polyhydric alcohols, for example methanol, octadecanol, 1,6-hexanediol, neopentylglycol thiodiethyleneglycol, diethylene glycol, triethyleneglycol pentaerytritol, trishydroxyethyl isocyanurate or dihydroxyethyloxalyldiamide.

9. Amides of β-(3,5-di-tert-butyl-4-hydroxyphenyl)-propionic acid for example,
N,N'-bis(3,5-di-tert-butyl-4-hydroxyphenylpropionyl)-hexamethylenediamine
N,N'-bis(3,5-di-tert-butyl-4-hydroxyphenylpropionyl)-trimethylenediamine
N,N'-bis(3,5-di-tert-butyl-4-hydroxyphenylpropionyl)-hydrazine.

EXAMPLES OF AMINE ANTIOXIDANTS

N,N'-diisopropyl-p-phenylenediamine
N,N'-di-sec-butyl-p-phenylenediamine
N,N'-bis(1,4-dimethylpentyl)-p-phenylenediamine
N,N'-bis(1-ethyl-3-methylpentyl)-p-phenylenediamine
N,N'-bis(1-methylheptyl)-p-phenylenediamine
N,N'-dicyclohexyl-p-phenylenediamine
N,N'-diphenyl-p-phenylenediamine
N,N'-di(naphthyl-2-)-p-phenylenediamine
N-isopropyl-N'-phenyl-p-phenylenediamine
N-(1,3-dimethylbutyl)-N'-phenyl-p-phenylenediamine
N-(1-methylheptyl)-N'-phenyl-p-phenylenediamine
N-cyclohexyl-N'-phenyl-p-phenylenediamine
bis-4-(toluenesulfonamidophenyl)amine
N,N'-dimethyl-N,N'di-sec-butyl-p-phenylenediamine
diphenylamine
4-isopropoxydiphenylamine
N-phenyl-1-naphthylamine
N-phenyl-2-naphthylamine
octylated diphenylamine
4-n-butylaminophenol
4-n-butyrylaminophenol
4-nonanoylaminophenol
4-dodecanoylaminophenol
4-octadecanoylaminophenol
bis(4-methoxyphenyl)amine
2,6-di-tert-butyl-4-dimethylaminomethylphenol
2,4-diaminodiphenylmethane
4,4'-diaminodiphenylmethane
N,N,N'N'-tetramethyl-4,4'-diaminodiphenylmethane
1,2-bis(phenylamino)ethane
1,2-bis[(2-methylphenyl)amino]ethane
1,3-bis(phenylamino)propane
(o-tolyl)biguanide
bis-[4-(1',3'-dimethylbutyl)phenyl]amine Examples of Metal Deactivators are for copper, e.g.: benzotriazole, tetrahydrobenzotriazole, 2-mercaptobenzotriazole, 2,5-dimercaptothiadiazole, salicylidene propylenediamine, salts of salicylaminoguanidine.

Examples of Rust Inhibitors are a) Organic acids, the esters, metal salts and anhydrides thereof, e.g.: N-oleylsarcosine, sorbitan monooleate, lead naphthenate, dodecenylsuccinic anhydride, monoalkenyl succinate, 4-nonylphenoxyacetic acid.

b) Nitrogen-containing compounds, for example:

I. Primary, secondary or tertiary aliphatic or cycloaliphatic amines and amine salts of organic and inorganic acids, for example oil-soluble alkylammonium carboxylates.

II. Heterocyclic compounds, e.g. substituted imidazolines and oxazolines.

c) Phosphorous-containing compounds, for example: amine salts of phosphoric acid partial esters.

d) Sulfur-containing compounds, for example: barium dinonylnaphthalenesulfonates, calcium petroleum sulfonates.

Examples of viscosity index improvers are polymethylacrylates, vinyl pyrrolidone/methacrylate copolymers, polybutene, olefin copolymers, styrene/acrylate copolymers.

Examples of pour-point depressors are polymethacrylates, alkylated naphthalene derivatives.

Examples of dispersants/surfactants are polybutenylsuccinimides, polybutenylphosphonic acid derivatives, basic magnesium, calcium and barium sulfonates and phenolates.

Examples of anti-wear additives are compounds which contain sulfur and/or phosphorous and/or halogen, such as sulfurised vegetable oils, zinc dialkyldithiophosphates, tritolylphosphate, chlorinated paraffins, alkyl disulfides and aryl disulfides.

PREPARATORY EXAMPLES 1–4

The salts listed in the following table are obtained by reacting together appropriate molar amounts of methylphosphonic acid and primary amine.

TABLE

| Compound | Formula | Properties |
|---|---|---|
| 1 | $CH_3-P(=O)(OH)_2 \cdot [iso-C_{13}H_{27}NH_2]^{1)}$ | yellow viscous fluid $n_D^{20} = 1.4612$ |
| 2 | $CH_3-P(=O)(OH)_2 \cdot [iso-C_{13}H_{27}NH_2]^{1)}$ + 25% of paraffin oil | yellow viscous fluid |

TABLE-continued

| Compound | Formula | Properties |
|---|---|---|
| 3 | $CH_3-P(=O)(OH)_2 \cdot [iso-C_{13}H_{27}NH_2]_{1.5}{}^{1)}$ | yellow viscous fluid |
| 4 | $CH_3-P(=O)(OH)_2 \cdot [iso-C_{20}H_{41}NH_2]_{1.5}{}^{2)}$ | yellow viscous fluid |

[1] PRIMENE 81-R ®
[2] PRIMENE JM-T ®

EXAMPLE 5

The weld load (WL) and the wear scar diameter (WSD) are determined using the Shell four-ball machine (IP 239/73, Extreme Pressure and Wear Lubricant Test for Oils and Greases, Four-Ball Machine) as a function of the concentration of the extreme pressure additive.

WL = weld load: the load at which the 4 balls become welded together within 10 seconds WSD = wear scar diameter: the average diameter of the scars produced on the 3 immobile balls after 10 minutes at a load of 400N.

The test fluid employed is a mineral oil of viscosity class ISO VG 100. The results are reported in the following table.

TABLE

| Additive (compound) | concentration (% by weight) | W.L. (N) | WSD after 10 min. and 400 N (mm) |
|---|---|---|---|
| — | — | 1450 | — |
| 1 | 1.0 | 3750 | 0.50 |
| 1 | 2.0 | 6500 | 0.53 |
| 1 | 5.0 | 9500 | — |
| 1 | 10.0 | 9500 | — |

What is claimed is:

1. A lubricant composition consisting essentially of a lubricant and as an extreme pressure and antiwear additive, an effective amount of a compound of the formula

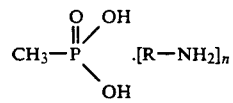

wherein n is an integer from 1.0 to 2.2 and R is a straight chain or branched $C_8-C_{30}$ alkyl which may be interrupted by 1 to 5 sulfur atoms, or R is a straight chain or branched $C_8-C_{30}$ alkenyl.

* * * * *